(12) United States Patent
Zenge

(10) Patent No.: US 8,867,756 B2
(45) Date of Patent: Oct. 21, 2014

(54) AUSCULTATION APPARATUS WITH TWO OPTICAL MICROPHONES

(75) Inventor: Michael Zenge, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 739 days.

(21) Appl. No.: 12/909,905

(22) Filed: Oct. 22, 2010

(65) Prior Publication Data
US 2011/0098555 A1 Apr. 28, 2011

(30) Foreign Application Priority Data

Oct. 26, 2009 (DE) .................. 10 2009 050 663

(51) Int. Cl.
A61B 7/04 (2006.01)
A61B 7/00 (2006.01)
G01R 33/28 (2006.01)
G01R 33/567 (2006.01)
A61B 5/00 (2006.01)
A61B 5/055 (2006.01)

(52) U.S. Cl.
CPC .............. G01R 33/283 (2013.01); A61B 7/04 (2013.01); A61B 5/7285 (2013.01); A61B 5/7207 (2013.01); A61B 5/055 (2013.01); G01R 33/5673 (2013.01)
USPC .......................................... 381/67; 600/586

(58) Field of Classification Search
USPC .......................................... 381/67; 600/586
See application file for complete search history.

(56) References Cited

U.S. PATENT DOCUMENTS

| 5,022,405 | A * | 6/1991 | Hok et al. ..................... 600/528 |
| 5,539,831 | A * | 7/1996 | Harley ............................ 381/67 |
| 7,082,202 | B1 | 7/2006 | Orten |
| 2006/0159142 | A1 * | 7/2006 | Sanchez ..................... 372/38.02 |
| 2008/0013747 | A1 * | 1/2008 | Tran ................................. 381/67 |
| 2008/0107292 | A1 | 5/2008 | Kornagel |
| 2009/0232323 | A1 * | 9/2009 | Berk et al. ....................... 381/67 |
| 2010/0139405 | A1 * | 6/2010 | Melikechi et al. .............. 73/655 |

FOREIGN PATENT DOCUMENTS

DE 69918713 T2 7/2005
DE 102006046700 A1 4/2008

OTHER PUBLICATIONS

MediLexicon, 'Cardiac Gating', 2006.*
Frauenrath Tobias et al., "The MR-stethoscope: safe cardiac gatingfree of interference with electro-magnetic fields at 1.5 T, 3.0 T and 7.0 T" Journal of Cardiovascular Magnetic Resonance 2009, 11(Suppl 1), pp. 63-64; http://jcmr-online.com/supplements/11/S1.
Henneberg et al: << Remote auscultatory patient monitoring during magnetic resonance imaging, J Clin Monit 1992, pp. 37-43.
Jalel Chebil et al., "Classification of Heart Sound Signals Using Discrete Wavelet Analysis", International Journal of Soft Computing 2(1), 2007, pp. 37-41.
Yong-Joo Chung, "Classification of Continuous Heart Sound Signals Using the Ergodic Hidden Markow Model", Marti et al (Eds.): IbPRIA 2007, Paet I, LNCS 4477, 2007, pp. 563-570. Springer-Verlag Berlin Heidelberg.
Fraunhofer Magazin, Kapitel "Spektrum", 2004, pp. 6-7.

* cited by examiner

Primary Examiner — Ahmad Matar
Assistant Examiner — Katherine Faley

(57) ABSTRACT

An auscultation apparatus including an optical microphone is proposed. Optical microphones can reliably acquire sounds of the most disparate frequencies even in an environment permeated by electromagnetic fields, without influencing said fields. Such an optical microphone of an auscultation apparatus can be disposed inside a medical examination and diagnostic device during operation. Given a suitable arrangement, both the heart sounds and the respiratory sounds of a patient can be recorded and monitored already with just one optical microphone.

11 Claims, 1 Drawing Sheet

AUSCULTATION APPARATUS WITH TWO OPTICAL MICROPHONES

CROSS-REFERENCE TO RELATED APPLICATIONS

This application claims priority of German application No. 10 2009 050 663.2 filed Oct. 26, 2009, which is incorporated by reference herein in its entirety.

FIELD OF THE INVENTION

The invention relates to an auscultation apparatus, an auscultation method, and a medical examination and diagnostic device.

BACKGROUND OF THE INVENTION

In a multiplicity of examinations of patients using advanced examination and diagnostic devices, for example magnetic resonance scanners, it is useful or even essential to monitor and/or record a patient's vital functions, e.g. his/her breathing and heartbeat, during the examination.

This may be necessary on the one hand for monitoring the patient's condition, in particular if the patient has been sedated or anesthetized. On the other hand it is necessary in many modern-day examination procedures to synchronize an acquisition of data included as part of the examination with a movement caused by the patient's vital functions. In particular in the case of magnetic resonance examinations a synchronization of said type is frequently used in order to minimize motion artifacts in acquired images and/or in order to enable an image to be acquired at a desired time instant during the movement, e.g. respiratory movement or heartbeat.

Monitoring the vital functions is not, however, possible simply as a matter of course if the patient is situated inside the examination and diagnostic device during the examination so that he/she cannot be observed from outside.

For this purpose it is known for example to measure ECG signals by means of an ECG measuring instrument and use them for generating trigger signals for the data acquisition during the examination (ECG: electrocardiogram). During the imaging information about the cardiac phase is obtained by way of the ECG signal so that the imaging can be synchronized with the activity of the heart. ECG measuring instruments are also used during an examination of a patient by means of a magnetic resonance device for in-situ recording of ECG signals. In this case, however, due to the strong gradient fields and high-frequency fields used for imaging in a magnetic resonance device, operation therein imposes special demands on the ECG measuring instrument in order to prevent mutual interference between magnetic resonance device and ECG measuring instrument. ECG measuring instruments which are magnetic resonance compatible within the above-cited meaning are commercially available. However, determining so-called "R waves" in the recorded ECG signals, which is essential for reliable triggering, is still not reliably possible e.g. due to interference voltages that are generated by electromagnetic alternating fields and coupled as noise into the ECG signal acquired by the ECG electrodes and overlay the actual ECG signal.

In order to register respiratory movements it is known to use so-called "respiratory belts" which are strapped around the patient's torso and transmit a compression of the pneumatically operating respiratory belt caused by the respiratory movement via a tubing system to a recording device located outside of the medical examination and diagnostic device. However, the accuracy of the thus detected respiratory movement is not always sufficient for reliable monitoring or for triggering data acquisitions.

Alternatively it is known in MR examinations (MR: Magnetic Resonance) to determine the respiratory movements of a patient by means of so-called "navigator measurements" which are performed in addition to the actual MR measurement. However, this requires intricate planning of the measurements and increases the overall exposure of the patient to irradiated energy.

The publication by Henneberg S. et al: "Remote auscultatory patient monitoring during magnetic resonance imaging", J Clin Monit 1992, 8:37-43, discloses a stethoscope having an acoustic signaling line for monitoring the respiratory sounds and heart sounds of sedated or anesthetized patients during an MR examination.

A stethoscope that has an acoustic signaling line and is used for triggering MR scans is known from the publication by Frauenrath Tobias et al: "The MR stethoscope: safe cardiac gating free of interference with electro-magnetic fields at 1.5 T, 3.0 T and 7.0 T", Journal of Cardiovascular Magnetic Resonance 2009, 11(Suppl 1), pp. 63-64.

An acoustic signaling line is subject to strong attenuation effects, with the result that the quality of the transmitted signals deteriorates rapidly as the length of the signaling line increases.

SUMMARY OF THE INVENTION

It is therefore an object of the present invention to disclose an auscultation apparatus, an auscultation method, and a medical examination and diagnostic device by means of which it is reliably possible to monitor and/or record a patient's vital functions also inside a medical examination and diagnostic device and also during an examination, without the above-cited disadvantages.

The object is achieved by an auscultation apparatus, an auscultation method, and a medical examination and diagnostic device as claimed in the claims.

An auscultation apparatus according to the invention includes an optical microphone. Optical microphones can reliably record sounds and noises of the most disparate frequencies even in an environment permeated by electromagnetic fields, without influencing said fields. An optical microphone of said kind in an auscultation apparatus can be disposed inside a medical examination and diagnostic device during operation.

A method according to the invention for auscultating a patient during an examination by means of a medical examination and diagnostic device comprises the steps of:

acquiring sounds caused by the patient by means of an optical microphone, forwarding the acquired sounds by means of optical signal transmission lines to a data processing device, recording and/or analyzing the acquired sounds by means of the data processing device.

The analysis that can be performed by the data processing device can include in particular that the acquired sounds are stored and/or examined e.g. in respect of occurring repetition times, for instance by determining a repetition time as the time between two succeeding occurrences, of a repeatedly occurring sound, or also by determining a time instant at which a selected sound occurs.

In an exemplary embodiment a data processing device of the aforesaid kind can also be connected to a control unit of a medical examination and diagnostic device for the purpose of transmitting data.

In an exemplary embodiment the auscultation apparatus includes at least one second optical microphone. A second optical microphone enables e.g. further sounds, caused, say, by the examination, to be acquired and/or the sounds acquired by the first optical microphone to be subjected to a plausibility check. For that purpose the sounds acquired by the second optical microphone can, for example, likewise be transmitted via optical signal transmission lines to a data processing device. In particular the sounds acquired by the first and the second optical microphone can be transmitted to the same data processing device and e.g. processed together there.

A medical examination and diagnostic device according to the invention, in particular a magnetic resonance device, includes an aforementioned auscultation apparatus.

The advantages cited in relation to the auscultation apparatus apply analogously to the method and to the medical examination and diagnostic device.

BRIEF DESCRIPTION OF THE DRAWINGS

Further advantages and specifics of the present invention will emerge from the exemplary embodiments described herein below and with reference to the figures. The examples presented do not constitute any limiting of the invention.

DETAILED DESCRIPTION OF THE INVENTION

Figure 1:
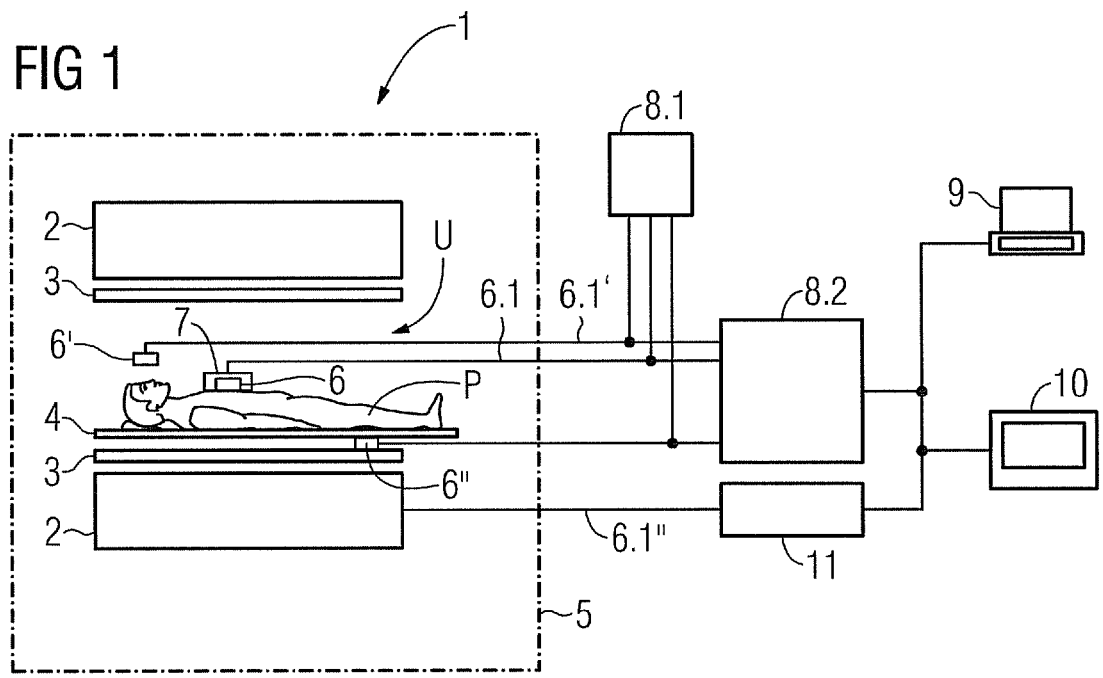
FIG. 1 is a schematic representation of an auscultation apparatus according to the invention in conjunction with a medical examination and diagnostic device.

FIG. 1 shows a schematic view of an auscultation apparatus comprising at least one optical microphone 6,6',6" in conjunction with a medical examination and diagnostic device 1, which in this instance is represented by way of example as a magnetic resonance device 1.

Figure 2:
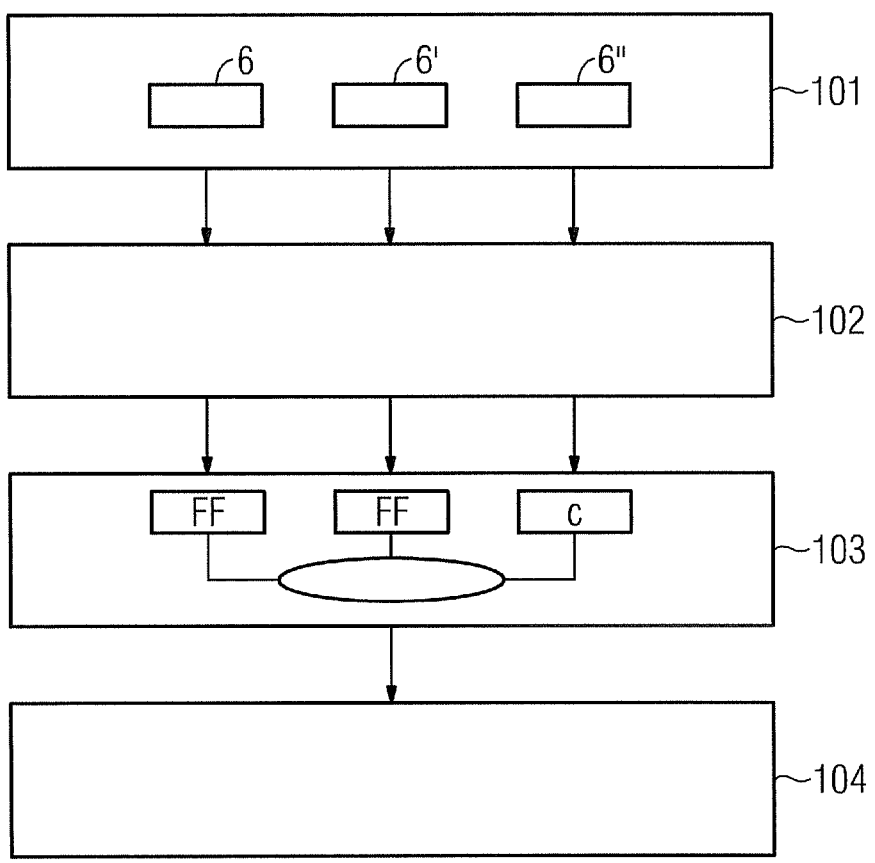
FIG. 2 is a schematic flowchart of a method according to the invention.

FIG. 2 shows a schematic flowchart of a method according to the invention. FIGS. 1 and 2 are described in more detail below.

The medical examination and diagnostic device 1 comprises a main magnet 2 and gradient coils 3 which can generate the electromagnetic fields necessary for an MR examination in an examination region U of the magnetic resonance device 1. In this arrangement the main magnet 2 and the gradient coils 3 enclose the examination region U into which a patient P can be introduced for the purpose of an MR examination, e.g. by means of a patient positioning table 4.

The main magnet 2 and the gradient coils 3 are usually disposed in a radio-frequency-shielded measurement chamber 5.

A control unit 11 controls the sequence of steps in an MR examination workflow, in particular an irradiation with the electromagnetic fields.

Since magnetic resonance devices are known per se, a description of further components and a more precise explanation of the functional interrelationships between said components will be omitted for the sake of clarity.

The at least one optical microphone 6,6',6" of the auscultation apparatus can be disposed inside the medical examination and diagnostic device 1 during operation and there e.g. pick up sounds caused by the patient. This is shown as step 101 in FIG. 2.

Conventional optical microphones comprise a sound-sensitive, reflecting membrane (not shown) onto which known light of a light source, for example a laser, is directed. Such a light source (not shown) can be disposed for example in a microphone control unit 8.1. The sound-sensitive membrane reflects the light as a function of a sound/noise impinging on the membrane, which means that e.g. the intensity of the reflected light is sound-dependent. The reflected light is transmitted to a data processing device 8.2 which includes e.g. a photodetector which converts the reflected light into an electrical signal that corresponds to an acquired sound. The light is transmitted from the light source to the membrane and from the membrane to the photodetector via optical signal transmission lines, e.g. fiber optic cables.

The at least one optical microphone 6,6',6" is connected to a data processing device 8.2 via optical signal transmission lines 6.1,6.1',6.1". This means that sounds acquired by the at least one optical microphone 6,6',6" can be transmitted to the data processing device 8.2 via the optical signal transmission lines 6.1,6.1',6.1". This forwarding of the acquired sounds to the data processing device 8.2 by means of optical signal transmission lines 6.1,6.1',6.1" is represented by step 102 in FIG. 2. The optical signal transmission lines 6.1,6.1',6.1" can be, for example, conventional optical waveguides, e.g. glass fiber cables. Optical waveguides of said type can transmit signals loss-free over several meters.

The data processing device 8.2 can record and/or analyze the acquired sounds supplied to it.

For example, the acquired sounds can, as already mentioned, be converted into electrical signals which can be analyzed more easily. For example, heart sounds such as described e.g. by Yong-Joo Chung in "Classification of Continuous Heart Sound Signals Using the Ergodic Hidden Markov Model", J. Marti et al. (Eds.): IbPRIA 2007, Part I, LNCS 4477, pp. 563-570, 2007, or by Jalel Chebil and Jamal Al-Nabulsi in "Classification of Heart Sound Signals Using Discrete Wavelet Analysis", International Journal of Soft Computing 2(1): 37-41, 2007, can be detected digitally. In addition to a digital analysis of the acquired sounds converted into electrical signals, analog circuitry can also be taken into consideration as suitable for filtering and e.g. a threshold value analysis of the acquired sounds before they are converted e.g. into electrical trigger signals, if the precision of such an analog analysis is sufficient for the desired purposes.

During the analysis of the acquired sounds it is conceivable in particular for e.g. respiratory sounds and/or heart sounds to be filtered out from the acquired sounds by way of filters FF of a corresponding frequency band, where e.g. heart sounds may lie in a frequency band from approx. 40 Hz to 200 Hz and respiratory sounds in a frequency band from approx. 200 Hz to 600 Hz corresponding to the possible frequencies of the respective periodic sounds. The analysis and/or recording of the acquired sounds are/is represented by step 103 in FIG. 2. By means of filtering of this kind ambient noises having a different frequency that were possibly likewise recorded can also be eliminated from the signal.

The data processing device 8.2 can also be connected to an input/output device 9 at which control commands for controlling the at least one optical microphone 6,6',6" of the data processing device 8.2 and/or control unit 11 of the medical examination and diagnostic device 1 can be input e.g. via a keyboard or a pointer input, such as, say, a computer mouse, and where applicable recorded and analyzed sounds can also be output. The data processing device 8.2 can furthermore be connected to a patient monitoring system 10 at which the recorded and analyzed sounds are output and e.g. monitored by qualified staff.

In this arrangement the data processing device 8.2 can also be disposed outside the measurement chamber 5 of the medical examination and diagnostic device 1. Toward that end e.g.

optical signal transmission lines 6.1,6.1',6.1" can be routed at a suitable point through the measurement chamber 5.

The auscultation apparatus can include in particular an auscultation head 7 which comprises the optical microphone 6 and is implemented in such a way that it can be arranged on the chest of a patient P. In such an arrangement e.g. heart sounds and/or respiratory sounds of the patient P can be acquired by means of the optical microphone 6. For example, the auscultation apparatus is a stethoscope having a bell as the auscultation head 7.

In one exemplary embodiment the auscultation apparatus comprises at least one second optical microphone 6' or 6". The at least one second optical microphone 6',6" is disposed for example at a distance from the first optical microphone 6. In this way other sounds or, as the case may be, sounds at another location can be acquired by the at least one second optical microphone 6',6" (see also FIG. 2, step 101). For example, a second optical microphone 6' can be disposed in the vicinity of the head of the patient P such that respiratory sounds can be acquired. In another exemplary embodiment a second microphone 6" can alternatively or additionally be disposed in the examination region U of the medical examination and diagnostic device 1 such that noises caused by the examination using the medical examination and diagnostic device 1 can be acquired.

The at least one second optical microphone 6',6" is likewise connected via optical signaling lines 6.1',6.1" to a (in particular the same) data processing device 8.2. Sounds acquired by the at least one second microphone 6',6" can thus be forwarded via the optical signal transmission lines 6.1',6.1" to the data processing device 8.2 (see also FIG. 2, step 102). This enables the sounds acquired by the first optical microphone 6 and at least one second optical microphone 6',6" to be processed together in the data processing device 8.2. It is of advantage in this case if the first optical microphone 6 and the second optical microphone 6" are operated jointly in stereo mode, i.e. on two channels. In this way interference and ambient noises can be effectively eliminated simply by taking the differential signal of the first and second channel.

Optical microphones are known from the company Optoacoustics Ltd., Israel, which are operated by hardware, wherein adjustment of the amplitudes of the microphones to +/−0.5 dB precisely can be achieved.

For example, undesirable noises, such as those caused, say, by the examination, e.g. can be computationally eliminated from the signal of the first optical microphone 6 by subtracting the signal, possibly converted as a constant scaling factor c, of the second optical microphone 6" which in this arrangement acquires only sounds caused by the examination, from the signal of the first optical microphone 6. Further links between signals of different optical microphones out of the optical microphones 6,6' and 6" are conceivable, as represented e.g. also in step 103 of FIG. 2.

Furthermore the data processing device 8.2 can be connected to a control unit 11 of a medical examination and diagnostic device 1 for the purpose of transmitting data.

Accordingly, the sounds recorded and/or analyzed by the data processing device 8.2 can be transmitted to the control unit 11 of the medical examination and diagnostic device 1 and be used there for controlling the medical examination and diagnostic device 1. This is represented by step 104 in FIG. 2.

In this way an examination of a patient P by means of the medical examination and diagnostic device 1 can be triggered e.g. on the basis of respiratory sounds and/or heart sounds acquired by means of the auscultation apparatus and analyzed in the data processing device 8.2 in such a way that e.g. scans taken using the medical examination and diagnostic device 1 are started in each case at a specific time instant within the movement cycle of the respiratory and/or cardiac movement of the patient P.

The examination can also be aborted e.g. during an examination of a sedated or anesthetized patient if deviations of the acquired respiratory sounds and/or heart sounds from predefined values are detected.

By virtue of the fact that no interactions with electromagnetic fields are present the disclosed auscultation apparatus is suitable in particular for use in conjunction with magnetic resonance devices, since it is fully MR-compatible. The signal transmission performed by means of optical signaling lines can be realized practically without loss over long distances of up to 10 meters and more.

Given a suitable arrangement, the heart and respiratory sounds of a patient can be recorded and monitored already with just one optical microphone 6.

The invention claimed is:

1. An auscultation apparatus to be used during an examination by a medical examination and diagnostic device, comprising:
    an optical microphone arranged in a single auscultation head of the auscultation apparatus for acquiring sounds caused by a patient during the examination;
    at least one second optical microphone not arranged in the single auscultation head of the auscultation apparatus and disposed at a distance from the optical microphone during the examination and inside an examination region of the medical examination and diagnostic device for acquiring noise caused by using the medical examination and diagnostic device during the examination; and
    a data processing device connected to the optical microphone and the at least one second optical microphone for analyzing the sounds,
    wherein the data processing device analyzes the sounds in occurring repetition times for determining a time instance at which a selected sound occurs for triggering the medical examination and diagnostic device at the time instance, and
    wherein the data processing device converts the noise acquired by the at least one second optical microphone as a constant scaling factor, and
    wherein the data processing device subtracts the converted constant scaling factor from the sounds acquired by the optical microphone to eliminate the noise caused by using the medical examination and diagnostic device during the examination from the sounds caused by the patient during the examination.

2. The auscultation apparatus as claimed in claim 1, wherein the auscultation head is disposed on a chest of the patient.

3. The auscultation apparatus as claimed in claim 1, wherein the optical microphone is connected to the data processing device via an optical signal transmission line.

4. The auscultation apparatus as claimed in claim 1, wherein the data processing device is connected to a control unit of a medical examination and diagnostic device.

5. The auscultation apparatus as claimed in claim 1, wherein the auscultation apparatus is a stethoscope.

6. The auscultation apparatus as claimed in claim 1, wherein the data processing device jointly operates the sounds acquired by the optical microphone and the noises acquired by the at least one second optical microphone in a stereo mode on different channels.

7. A method for auscultating a patient during an examination by a medical examination and diagnostic device, comprising:
- acquiring sounds caused by the patient by an optical microphone arranged in a single auscultation head of the auscultation apparatus;
- simultaneously acquiring noises caused by using the medical examination and diagnostic device during the examination by at least one second optical microphone not arranged in the single auscultation head of the auscultation apparatus and disposed at a distance from the optical microphone and inside an examination region of the medical examination and diagnostic device;
- forwarding the sounds and the noises to a data processing device; and
- analyzing the sounds and the noises by the data processing device;
- wherein the data processing device analyzes the sounds in occurring repetition times for determining a time instance at which a selected sound occurs for triggering the medical examination and diagnostic device at the time instance,
- wherein the data processing device converts the noise acquired by the at least one second optical microphone as a constant scaling factor, and
- wherein the data processing device subtracts the converted constant scaling factor from the sounds acquired by the optical microphone to eliminate the noise caused by using the medical examination and diagnostic device during the examination from the sounds caused by the patient during the examination.

8. The method as claimed in claim 7, wherein the sounds acquired by the optical microphone and the noises acquired by the at least one second optical microphone are processed together in the data processing device.

9. The method as claimed in claim 8, wherein the data processing device subtracts the sounds acquired by the optical microphone and the noises acquired by the at least one second optical microphone from each other.

10. A medical examination and diagnostic device for examining a patient, comprising:
- an auscultation apparatus comprising:
  - an optical microphone arranged in a single auscultation head of the auscultation apparatus for acquiring sounds caused by a patient during an examination;
  - at least one second optical microphone not arranged in the single auscultation head of the auscultation apparatus and disposed at a distance from the optical microphone and inside an examination region of the medical examination and diagnostic device for acquiring noise caused by using the medical examination and diagnostic device during the examination; and
  - a data processing device connected to the optical microphone and the at least one second optical microphone for analyzing the sounds,
  - wherein the data processing device analyzes the sounds in occurring repetition times for determining a time instance at which a selected sound occurs; and
- a control unit for triggering the medical examination and diagnostic device at the time instance,
- wherein the data processing device converts the noise acquired by the at least one second optical microphone as a constant scaling factor, and
- wherein the data processing device subtracts the converted constant scaling factor from the sounds acquired by the optical microphone to eliminate the noise caused by the using the medical examination and diagnostic device during the examination from the sounds caused by the patient during the examination.

11. The medical examination and diagnostic device as claimed in claim 10, wherein the medical examination and diagnostic device is a magnetic resonance device.

* * * * *